(12) United States Patent
Wyrobnik et al.

(10) Patent No.: US 9,415,093 B2
(45) Date of Patent: Aug. 16, 2016

(54) AGENT FOR USE IN THE CASE OF DISORDERS OF BLOOD SUGAR METABOLISM, INCLUDING DIABETES

(71) Applicant: PRO NATURA GESELLSCHAFT FUER GESUNDE ERNAEHRUNG MBH, Frankfurt am Main (DE)

(72) Inventors: Daniel Henry Wyrobnik, Frankfurt am Main (DE); Isaac Harry Wyrobnik, Frankfurt am Main (DE)

(73) Assignee: PRO NATURA GESELLSCHAFT FUR GESUNDE ERNAHRUNG MBG (DE)

( * ) Notice: Subject to any disclaimer, the term of this patent is extended or adjusted under 35 U.S.C. 154(b) by 143 days.

(21) Appl. No.: 14/140,600

(22) Filed: Dec. 26, 2013

(65) Prior Publication Data

US 2014/0286924 A1    Sep. 25, 2014

Related U.S. Application Data

(63) Continuation of application No. 12/094,684, filed as application No. PCT/EP2006/011232 on Nov. 23, 2006, now abandoned.

(60) Provisional application No. 60/757,425, filed on Jan. 10, 2006, provisional application No. 60/831,175, filed on Jul. 17, 2006.

(30) Foreign Application Priority Data

Nov. 23, 2005  (DE) .......................... 10 2005 056 103
Dec. 20, 2005  (DE) .......................... 10 2005 061 329
Jan. 5, 2006   (DE) .......................... 10 2006 001 017
Mar. 27, 2006  (DE) .......................... 10 2006 014 424

(51) Int. Cl.
| | | |
|---|---|---|
| C12N 9/00 | (2006.01) | |
| C12N 9/92 | (2006.01) | |
| A61K 38/44 | (2006.01) | |
| A61K 38/54 | (2006.01) | |
| A21D 8/04 | (2006.01) | |
| A21D 13/06 | (2006.01) | |
| A23L 1/00 | (2006.01) | |
| A23L 1/03 | (2006.01) | |
| A23L 1/307 | (2006.01) | |
| A61K 38/52 | (2006.01) | |
| A61K 38/47 | (2006.01) | |
| A23L 1/29 | (2006.01) | |

(52) U.S. Cl.
CPC ................ *A61K 38/54* (2013.01); *A21D 8/042* (2013.01); *A21D 13/062* (2013.01); *A23K 20/189* (2016.05); *A23L 1/0029* (2013.01); *A23L 1/034* (2013.01); *A23L 1/293* (2013.01); *A23L 1/307* (2013.01); *A61K 38/443* (2013.01); *A61K 38/47* (2013.01); *A61K 38/52* (2013.01); *A23V 2002/00* (2013.01)

(58) Field of Classification Search
CPC ...... C12N 9/00; C12N 9/0004; C12N 9/0006; C12N 9/92; A61K 38/44; A61K 38/52
See application file for complete search history.

*Primary Examiner* — Ruth Davis
(74) *Attorney, Agent, or Firm* — Daniel Feigelson; Fourth Dimension IP

(57) ABSTRACT

An agent for use in the case of disorders of blood sugar metabolism, including diabetes, is described, which reduces the glucose content of food and other substances with the help of 5-D-fructose dehydrogenase and glucose isomerase.

9 Claims, No Drawings

AGENT FOR USE IN THE CASE OF DISORDERS OF BLOOD SUGAR METABOLISM, INCLUDING DIABETES

This is a continuation of U.S. Ser. No. 12/094,684, which was filed as a 35 U.S.C. §371 application of PCT/EP2006/011232, filed Nov. 23, 2006, and claims the benefit under 35 U.S.C. §120 of said PCT application, and further claims the benefit under 35 U.S.C. §119(e) of U.S. Provisional Patent Applications U.S. Ser. No. 60/757,425, filed on Jan. 10, 2006 and U.S. Ser. No. 60/831,175, filed on Jul. 17, 2006.

The present invention relates to the use of an agent in the case of diabetes, which reduces the content of glucose in food and other substances consumed. In the context of this application, the term "diabetes" means all forms of disorders of blood sugar metabolism, also of the mild type, including all forms of diabetes, such as diabetes type I, including LADA diabetes (latent autoimmune diabetes in adults), diabetes type II, pregnancy-induced diabetes and impaired glucose tolerance. Accordingly, the invention is also suitable for persons who only have minor disorders of blood sugar metabolism and, therefore, are not (yet) referred to as diabetics in the medical sense.

According the invention the term "agent" includes a pharmaceutical composition, a medical device, a foodstuff and a special foodstuff.

According to the present invention, the terms food and foodstuff are used as synonyms. They mean to also include feed in the sense of animal feed. In the context of this application special foodstuffs are foodstuffs for particular nutritional uses, foods for special medical purposes, medical foods, food supplements, dietary supplements, dietetic food supplements, health foods, nutraceuticals and food additives. In the context of this application the term foodstuff means to include special foodstuffs as used herein, where applicable.

In the context of this application the term "glucose containing" refers to all substances and foodstuffs that either contain glucose in pure form or from which glucose can be released in the digestive tract. The glucose content of substances and foodstuffs refers to all the glucose in a glucose containing food or substance in whatever form (e.g. also as part of sucrose) it is contained in such a food or substance. From sucrose, glucose and fructose are released in equal parts by enzymatic cleavage in the intestines. In the context of this application the term "fructose containing" refers to all substances and foodstuffs that either contain fructose in pure form or from which fructose can be released in the digestive tract. The fructose content of substances and foodstuffs refers to all the fructose in a fructose containing food or substance in whatever form (e.g. also as part of sucrose) it is contained in such a food or substance.

Diabetes is an extremely wide-spread problem and the incidence of diabetes has constantly increased in Western Europe and North America. The two most important forms are diabetes type I (approx. 5 to 10%) and diabetes type II (approx. 90%). In the Federal Republic of Germany, for example, more than 9.9 million people suffer from diabetes of which approx. 3.9 million people suffer from the so-called impaired glucose tolerance. The consequences of diabetes are an increase in the level of blood glucose, glucosuria and later sequelae of the increased level of blood glucose in different organ systems, disorders of lipid metabolism, etc. Depending on whether it is a question of the various damage caused by average blood sugar values being too high over many years, such as to the eyes, kidneys and nerves, or damage caused by short-term blood sugar peaks, such as premature damage to the walls of the large arterial vessels, one refers to micro- or macro-angiopathic sequelae. The list of possible complications and late damage caused by diabetes is long and they are described in detail in the specialist literature.

Until now, therapies for disorders of blood sugar metabolism have basically been limited to increasing the content of insulin in the blood (by administering insulin or by enhancing the excretion of insulin) and enhancing the efficiency of insulin. An alternative approach is to delay the uptake of carbohydrates (agent for delaying absorption), but this leads to abdominal pain due to the bacterial degradation of carbohydrates that accumulate in the lower sections of the intestines. Despite all methods found to date for treating diabetes, there is still a need for agents that prevent or reduce the increase in the level of blood sugar as a result of the intake of glucose containing foods and substances, without placing a burden on the body.

An agent that would reduce the absorbed amount of glucose would thus satisfy an extremely wide-spread and pressing need which has existed for decades, since sufferers have considerable difficulties with "individual adjustment", i.e. with the exact adjustment of the dose of insulin in relation to the intake of carbohydrates. These difficulties remain, despite the variety of available medicaments and glucose free dietetic foodstuffs especially for diabetics, who are already very limited in the choice of foodstuffs they can eat. Such an agent would overcome the prejudice widely held in the specialist world and among those suffering from diabetes that a low-carbohydrate diet has to be maintained and that a considerable change in nutritional habits is necessary, and would also mean a significant improvement and dramatic development in the therapeutic and nutritional options in diabetes. Such an agent would also put an end to the as yet fruitless efforts of the specialist world to find an agent to treat diabetes which can be administered broadly, easily, and long-term, without causing side effects. This would apply all the more to an agent which, in addition, has no negative effects on health.

Thus, there is provided in accordance with embodiments of the present invention an agent that significantly reduces the usable content of glucose in food, in particular for facilitating the in-take of foodstuffs that normally contain glucose also in the case of diabetes, without resulting in negative effects on health. There is also provided in accordance with embodiments of the invention an agent to make it possible for diabetics to eat foodstuffs which until now were not allowed to them due to their glucose content or the eating of which was associated with negative effects for the sufferers' health. Moreover, in accordance with embodiments of the invention there is provided an agent that can reduce or prevent the associated negative effects on health after the intake of glucose in diabetes. There is also provided in accordance with embodiments of the invention an agent that can reduce or prevent an increase in the level of blood glucose in diabetes after the intake of glucose containing food.

Therefore, the subject matter of the invention is an agent that can be used for the curative or prophylactic treatment of diabetes, for diagnosis of diabetes, for reducing the bioavailability of glucose and/or fructose in the human or animal body, for reducing the glucose content and/or the fructose content in a foodstuff, and/or for preventing or at least reducing an increase in the level of blood glucose after the intake of glucose containing food.

The agent contains 5-D-fructose dehydrogenase (syn. fructose 5-dehydrogenase) and glucose isomerase. The enzyme 5-D-fructose dehydrogenase effects the conversion of fructose into 5-keto-D-fructose Glucose isomerase has the property of converting glucose into fructose and vice versa with an equilibrium concentration of approximately 50% glucose and 50% fructose. In the context of this application, a 5-D-fructose dehydrogenase is an enzyme that can catalyze the dehydrogenation of fructose to 5-keto-D-fructose. A glucose isomerase, in the context of this application, is an enzyme that is able to transform glucose into fructose. This conversion can also be brought about, for example, by a xylose isomerase. Thus, such a xylose isomerase is, in the sense of this invention, also a glucose isomerase. A possible method for the production of a xylose isomerase is, for example, described in Yamanaka, Biochimica et Biophysika Acta, Volume 151 (3), 1968, 670-680, "Purification, Crystallization and Properties of the D-Xylose Isomerase from *Lactobacillus brevis*" and in Yamanaka, Methods in Enzymology, Volume 41, 1971, 466-471, "D-Xylose Isomerase from *Lactobacillus brevis*".

The effect of the enzyme combination according to the present invention will be explained using starch as an example. Since in particular glucose is released from starch as a monosaccharide during digestion, this is transformed by the glucose isomerase into fructose, which is then converted by the 5-D-fructose dehydrogenase into 5-keto-D-fructose, which cannot be metabolized by the body. Thus, the 5-D-fructose dehydrogenase prevents the establishment of the above-mentioned equilibrium. Therefore, said glucose isomerase will convert glucose into fructose, which itself will be dehydrogenated into 5-keto-D-fructose by the 5-D-fructose dehydrogenase, until no further glucose is present in the food or food pulp.

Also in the case of sucrose, a reduction of glucose can be achieved with this combination agent. Fructose which is released from sucrose during digestion is converted into 5-keto-D-fructose by the 5-D-fructose dehydrogenase, as described above. The Glucose isomerase then tries to balance out the resulting "disequilibrium" by converting glucose into fructose. As in the case of starch, this conversion process continues until no further glucose is present in the food pulp. It is possible that part of the glucose has already been absorbed by then. However, the total amount of glucose that will be absorbed from a sugar containing meal will be significantly reduced with the help of the invention disclosed herein. Depending on the level of enzyme activity per dose unit and the amount of the glucose content of the respective meal, it is possible to influence the amount of glucose absorbed by the body. If desired, according to the present invention, it is also possible to achieve a complete or virtually complete elimination of glucose.

Thus, the invention is based on the fact that the glucose contained in the consumed carbohydrates, such as sucrose, or released from them in the intestines, is no longer available for the undesired absorption from the intestines and release into the bloodstream. This is achieved by consuming a mixture of the two enzymes glucose isomerase and 5-D-fructose dehydrogenase before, shortly before, with, shortly after or after consumption of glucose-containing-foods, by conversion of glucose to fructose and its subsequent dehydrogenation to 5-keto-D-fructose. The enzymes transform glucose into fructose and the fructose into 5-keto-D-fructose, until no further glucose is present. The dosage of the enzymes added may be selected in such a way that, also in the case of an intake of larger amounts of glucose, the reaction can take place at an appropriate rate.

Furthermore, the enzyme combination according to the present invention also has the effect of reducing the intake of calories, which is desired in the case of diabetes, since the enzyme combination, as described above, converts carbohydrates contained in the food into 5-keto-D-fructose, which is significantly less caloric than fructose and glucose. In particular, this is desired in the case of diabetes type II, since diabetics often suffer from obesity, hypertension and disorders of lipid metabolism. In addition, the enzyme combination according to the present invention has the effect that it can convert fructose originating from fructose containing substances and foodstuffs into 5-keto-D-fructose, which is desired in the case of diabetes. Although fructose is used in large amounts as a sweetener in food for diabetics, and fructose is generally regarded as being well-tolerated and harmless for diabetics, there is an ongoing debate among specialists that the intake of fructose is also undesirable and contraindicated in diabetes and should be limited, in particular due to the utilizable calorie content of fructose. In contrast to glucose, fructose is metabolized independently of insulin. Since insulin influences the occurrence of the sensation of satiation indirectly, fructose does not eliminate the appetite, obesity may easily occur as a result of the extensive use of fructose as a sweetener. Free fructose in large amounts may also favour hypertension. It also influences the lipid profile (blood lipids) in an unfavourable way, since in larger amounts it promotes the synthesis of lipids and thus increases the postprandial serum triglycerides. Therefore, especially larger amounts of fructose should not be consumed by diabetics.

Patients with metabolic syndrome are advised in particular not to consume beverages that are sweetened with HFCS (high fructose corn syrup) or sucrose.

Therefore, a subject matter of the invention is an agent for use in the case of diabetes which contains a glucose isomerase and a 5-D-fructose dehydrogenase.

Further, a subject matter of the invention is an agent that reduces the bioavailability of glucose in the human or animal body with the help of a glucose isomerase in combination with a 5-D-fructose dehydrogenase.

Also, a subject matter of the invention is an agent for reducing the utilizable content of glucose of food, which contains a glucose isomerase in combination with a 5-D-fructose dehydrogenase.

Also, a subject matter of the invention is an agent for preventing or reducing an increase of the level of blood glucose in the case of diabetes after the intake of glucose containing food.

A further subject matter of the invention is the use of a glucose isomerase in combination with a 5-D-fructose dehydrogenase in the case of diabetes and in the case of health problems and diseases associated with diabetes.

According to the present invention, a 5-D-fructose dehydrogenase in combination with glucose isomerase can also be used for reducing the utilizable content of glucose in a foodstuff.

In a particularly easy way, the invention facilitates the transformation of glucose in a foodstuff into a form that does not result in an increase in the level of blood glucose. Thus, the invention enables diabetics to consume foodstuffs that they have had to avoid up till now, due to their glucose content.

According to the present invention, 5-D-fructose dehydrogenase in combination with glucose isomerase is further mentioned for use in medicine, for example, as a pharmaceutical composition. Accordingly, a subject matter of the invention is also a product that consists of 5-D-fructose dehydrogenase in combination with glucose isomerase or contains 5-D-fructose dehydrogenase in combination with glucose isomerase, beside one or more other active ingredients, for use in a medical method, especially in a method for the therapeutic treatment of the human or animal body. In the context of this application, a pharmaceutical composition is a product, especially a substance or a substance mixture, for use in a method for surgical or therapeutic treatment of the human or animal body and in diagnostic methods that are performed on the human or animal body. Thus, in the sense of the invention, pharmaceutical compositions are also products, in particular sub-stances or substance mixtures, that are meant or suitable for curing, alleviating, preventing or determining diabetes.

The term "treating" when used in connection with the foregoing disorders includes amelioration, prevention or relief from the symptoms and/or effects associated with these disorders and includes the prophylactic administration of an enzyme or a mixture thereof to diminish the likelihood or seriousness of the conditions.

According to a further aspect, according to the present invention, a foodstuff is provided that contains glucose isomerase in combination with 5-D-fructose dehydrogenase. Further, according to the present invention, a foodstuff is provided that contains 5-D-fructose dehydrogenase in combination with glucose isomerase in an amount which is effective for converting fructose into 5-keto-D-fructose and glucose isomerase in an amount which is effective for transforming glucose into fructose. Such a foodstuff may be produced advantageously using a method for treating a foodstuff in which the foodstuff is placed in contact with a 5-D-fructose dehydrogenase in combination with glucose isomerase under such conditions under which the 5-D-fructose dehydrogenase can dehydrogenate fructose to 5-keto-D-fructose and the glucose isomerase can convert glucose into fructose. In contrast to otherwise untreated foodstuffs, such a foodstuff has a reduced content of glucose and therefore, for the first time, is suitable to be eaten by diabetics. Particularly advantageously, a foodstuff may be prepared by a method in which a glucose isomerase in combination with a 5-D-fructose dehydrogenase is added to the foodstuff in a manner in which the action of the two enzymes does not start until after the foodstuff has been consumed. Such a foodstuff that contains 5-D-fructose dehydrogenase and glucose isomerase has the same taste as an untreated food-stuff and is, for the first time, suitable to be eaten by diabetics, due to the reduced content of glucose which is established after consumption.

According to a further aspect, according to the present invention, 5-D-fructose dehydrogenase in combination with glucose isomerase is provided as a medical de-vice. Accordingly, the subject matter of the invention is also a medical device that consists of 5-D-fructose dehydrogenase in combination with glucose isomerase or contains 5-D-fructose dehydrogenase in combination with glucose isomerase, be-side one or more other active ingredients.

In the following, the invention will be described further in its various aspects.

5-D-fructose dehydrogenase is a compound that has been known for nearly 40 years, but has only been used for analytical purposes to date. Glucose isomerase is a compound that has been known for more than 40 years and has only been used for starch saccharification to date. In the industry, it is used for the conversion of glucose into fructose as well as for the conversion of fructose into glucose.

Until now, 5-D-fructose dehydrogenase has not been used in combination with glucose isomerase in the case of diabetes of humans or animals.

The agent according to the present invention can be taken orally prior to meals, immediately before meals, with meals or immediately after meals, so that it can exert its converting effect on glucose and dehydrogenating effect on fructose in the food pulp. The agent according to the present invention may contain the enzymes without further additives. However, it is preferable that the agent according to the present invention further contains additives that are pharmaceutically acceptable and/or acceptable for foodstuffs, such as for example extenders, binders, stabilizers, preservatives, flavourings, etc. Such additives are commonly used and well known for the production of pharmaceutical compositions, medical devices, food-stuffs, and special foodstuffs and the person skilled in the art knows which additives in which amounts are suitable for certain presentation forms. The agents according to the present invention may for example contain as additives dicalcium phosphate, lactose, modified starch, microcrystalline cellulose, maltodextrin and/or fiber-sol.

The agent according to the present invention can also be added to a foodstuff before its consumption. It can already be added to the foodstuff during production, with the aim that it exhibits its effect only after eating the foodstuff. This could also be achieved by microencapsulation, for example. With this, the utilizable glucose content of the foodstuff would be reduced without negatively affecting its taste. Therefore, preparations containing 5-D-fructose dehydrogenase and glucose isomerase are useful, which release this enzyme only in the digestive tract of a human or animal or let it become effective in another way, especially in the stomach or small intestine. Therefore, the invention can be used, for example, in the production of desserts, fruit preparations (e.g. apple sauce), jam, honey, chocolate and chocolate products, bakery products (e.g. biscuits and cakes), breads, pastas, vegetable dishes, potato dishes, ice cream, cereals, dairy products (e.g. fruit yogurt and pudding), fructose- and/or glucose-containing beverages, fructose- and/or glucose-containing sauces (e.g. tomato ketchup) and fructose- and/or glucose-containing sweeteners. For dishes that are boiled or baked, the agent according to the present invention could e.g. be mixed into or sprinkled onto them after cooling.

The agent according to the present invention can also be added to a foodstuff, to exert its effect after eating on the glucose originating from another foodstuff. An example of this would be the addition of the agent according to the present invention to a spread so that the reduction of the glucose that is contained in the bread and that can be used by the body occurs after the intake of the bread, without impairing its taste. Further examples would be mixed spices and mayonnaise for use with french fries.

The agent according to the present invention may also be used in immobilized form. This is especially useful for the treatment of liquid foodstuffs. For example, the enzymes can be embedded in a matrix which is permeable for glucose. If a glucose containing liquid foodstuff is allowed to flow along the enzyme containing matrix, then glucose is extracted from the foodstuff by the action of the enzymes and converted to 5-keto-D-fructose.

A subject matter of the present invention are also agents that, in addition to other active ingredients, also contain glucose isomerase in combination with 5-D-fructose dehydrogenase.

The agent may be formulated in any form which is suitable for the intended route of administration. A preferred route of administration is oral administration. For oral administration, the agent may be formulated for example in the form of capsules (coated or non-coated) containing powder, coated or non-coated pellets, granules or micro-/mini-tablets or in the form of tablets (coated or non-coated) pressed from powder, coated or non-coated pellets, dragées or micro-/mini-tablets. The agent may also be formulated for example in the form of gel caps or in liquid form as solution, drops, suspension or gel. The agent may also be formulated e.g. as dried or moist oral supplement. The formulation of the agent according to the present invention as powder is particularly suitable for admixing with foodstuff. The powder may be sprinkled onto a meal or mixed into a pulp or beverage. It is particularly beneficial, if the agent offered as bulk powder is packaged in single dosage amounts, such as in single bags or capsules, or if it is provided in a dosing dispenser.

For oral administration, the 5-D-fructose dehydrogenase in combination with glucose isomerase may be used with acceptable excipients and/or carriers.

The total amount of the carrier and/or excipient of an agent containing 5-D-fructose dehydrogenase and glucose isomerase is preferably between 5 and 99.9% by weight, more preferably between 10 and 80% by weight and even more preferably between 25 and 60% by weight of the composition.

Suitable excipients and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethyl cellulose, corn starch, modified starch, fibersol, gelatine, hy-droxypropylmethyl cellulose and the like (including mixtures thereof).

Preferable carriers include calcium carbonate, magnesium stearate, maltodextrin, dicalcium phosphate, modified starch, microcrystalline cellulose, fibersol, gelatine, hydroxypropylmethyl cellulose and mixtures thereof.

The various ingredients and the excipient and/or carrier may be mixed and formed into the desired form using common methods well known to the skilled person. The administration form according to the present invention which is suited for the oral route, such as e.g. tablet or capsule, may be coated with a coating which is resistant against low pH values (approximately pH 1 to 2.5) and which dissolves at a pH value of approximately 3.0 to 8.0, preferably at a pH value of 3.0 to 6.5 and particularly preferable at a pH value of 4.0 to 6.0. An optionally used coating should be in accordance with the pH optimum of the enzyme used and its stability at pH values to which the formulation will be exposed. Also a coating may be used which is not resistant to low pH values but which delays the release of the enzyme at low pH values. It is also possible to prepare the agent according to the present invention as coated (see above) pellets, granules or micro-/mini-tablets which can be filled into coated or non-coated capsules or which can be pressed into coated or non-coated tablets. Suitable coatings are, for example, cellulose acetate phthalate, cellulose derivates, shellac, polyvinylpyrrolidone derivates, acrylic acid, poly-acrylic acid derivates and polymethyl methacrylate (PMMA), such as e.g. Eudragit® (from Röhm GmbH, Darmstadt, Germany), in particular Eudragit® L30D-55. The coating Eudragit® L30D-55 is dissolved, for example, at a pH value of 5.5 and higher. If it is desired to release the enzyme already at a lower pH value, this may be achieved e.g. by the addition of sodium hydroxide solution to the coating agent Eudragit® L30D-55, because in this case carboxyl groups of the methacrylate would be neutralised. Therefore, this coating will be dissolved, for example, already at a pH value of 4.0 provided that 5% of the carboxyl groups are neutralised. The addition of about 100 g of 4% sodium hydroxide solution to 1 kg of Eudragit® L30D-55 would result in a neutralisation of about 6% of the carboxyl groups. Further details about formulation methods and administration methods can be found in the 21st edition of "Remington: The Science & Practice of Pharmacy", published 2005 by Lippincott, Williams & Wilkins, Baltimore, USA, in the Encyclopedia of Pharmaceutical Technology (Editor James Swarbrick) and in Prof. Bauer "Lehrbuch der Pharmazeutischen Technologie", 18th edition, published 2006 by Wissenschaftliche Verlagsgesellschaft (ISBN 3804-72222-9). The contents of these documents are incorporated herein by reference.

Other suitable acceptable carriers or adjuvants for use in the present invention include, but are not restricted to water, mineral oil, ethylene glycol, propylene glycol, lanolin, glyceryl stearate, sorbitan stearate, isopropyl myristate, isopropyl palmitate, acetone, glycerine, phosphatidylcholine, sodium cholate or ethanol.

The compositions for use in the present invention may also comprise at least one co-emulsifying agent which includes but is not limited to oxyethylenated sorbitan monostearate, fatty alcohols, such as stearyl alcohol or cetyl alcohol, or esters of fatty acids and polyols, such as glyceryl stearate.

The agents according to the present invention may be provided in a stabilized form. Generally, stabilization methods and procedures which may be used according to the present invention include any and all methods for the stabilization of chemical or biological material which are known in the art, comprising e.g. the addition of chemical agents, methods which are based on temperature modulation, methods which are based on irradiation or combinations thereof. Chemical agents that may be used according to the present invention include, among others, preservatives, acids, bases, salts, antioxidants, viscosity enhancers, emulsifying agents, gelatinizers, and mixtures thereof.

Usually, the industrial production of enzymes is performed in a technical fermentation way using suitable microorganisms (bacteria, moulds, fungi). Usually the strains are recovered from natural ecosystems according to a special screening protocol, isolated as pure cultures as well as improved in their properties with respect to the enzyme spectrum and biosynthesis performance (volume/time yield). Enzyme production may also be carried out by methods developed in the future.

5-D-fructose dehydrogenase is commercially available (e.g. Sigma-Aldrich or Toyobo Enzymes, Japan) and is usually prepared in a microbiological way with the help of the microorganism *gluconobacter industrius*. Glucose isomerase is also commercially available (e.g. Sigma-Aldrich or Novozymes A/S, Denmark) and usually prepared in a microbiological way with the help of the microorganism *streptomyces murinus*. However, the invention is not limited to the enzymes that are commercially available at the moment, but generally relates to enzymes that can catalyze the conversion of fructose—specifically or non-specifically—to 5-keto-D-fructose, and of glucose—specifically or non-specifically—to fructose. A person skilled in the art can prepare suitable further enzymes by conventional methods, for example by mutagenesis of the gene encoding 5-D-fructose dehydrogenase which is present in *gluconobacter industrius* or by mutagenesis of the gene encoding glucose isomerase in *streptomyces murinus*. The enzymes may also be prepared with the help of other microorganisms, such as fungi, in sufficient amounts and the required purities, also by the use of the genetic engineering methods which are presently known or may be developed in the future. For example, if it is desired to produce the enzymes with other microorganisms, then the genetic information of a microorganism which has been found initially by extensive screening and which has been proven to be a suitable source of the enzyme with the desired properties can be transferred to a microorganism which is normally used for the production of enzymes. Also the modification of the enzymes and the production of the enzymes by means of methods which are presently known or may be developed in the future in the area of industrial enzyme development and enzyme production, such as genetic engineering, is possible. The use and the manner of performing all these methods for developing and producing the enzyme(s) with the desired purities and activities and with the desired properties, in particular with respect to the stability of the enzyme(s) at various pH values, regarding the optimum of the pH value, the stability at various temperatures and temperature optimum, are well known to a person skilled in the art. The explanations in chapter 2 (page 82 to page 130) of the textbook "Lebensmittel-Biotechnologie and Ernährung" of Heinz Ruttloff, Jürgen Proll and Andreas Leuchtenberger, published by Springer Verlag 1997 (ISBN 3-540-61135-5) describe these methods in detail. These methods are also described in "Advances in Fungal Biotechnology for Industry, Agriculture, and Medicine" by Jan S. Tkacz, Lene Lange- and (published in 2004, ISBN 0-306-47866-8), in "Enzymes in Indus-try: Production and Applications" by Wolfgang Aehle (Editor), published in 2004, ISBN 3527295925 and in "Microbial Enzymes and Biotransformations" by Jose-Luis Barredo (Humana Press 2005, ISBN 1588292533). These documents are herewith incorporated into the patent application by reference. All this also applies to the enzymes mentioned below that can optionally be added to the agent according to the present invention.

The activity of 5-D-fructose dehydrogenase is defined in units (assay available e.g. from Sigma-Aldrich), whereby one unit is the amount of 5-D-fructose dehydrogenase that converts one micromole of D-fructose to 5-keto-D-fructose per minute at pH 4.5 and 37° C. Generally, the activity of 5-D-fructose dehydrogenase per dose unit should be between 10 and 5 million units, preferably between 25 and 2.5 million units and particularly preferably between 50 and 1 million units.

The activity of glucose isomerase should generally be between 0.01 and 100,000 GIU, preferably between 0.05 and 10,000 GIU and particularly preferably between 0.1 and 1,000 GIU per dose unit. One unit of this enzyme is defined as a glucose isomerase unit (GIU). One GIU converts 1 g of glucose into fructose at a pH value of 6.0 and at a temperature of 37° C. from a solution of initially 10% (percent by weight, i.e. 10 g of glucose+90 g of water) in 5 minutes.

The wide range of the above mentioned dosages may be explained by the fact that the agent according to the present invention can be applied in completely different types of diabetes in the whole range of different severities. Furthermore, the different dosages also result from the fact that strongly varying amounts of glucose are supplied, depending on the food in question.

The agent according to the present invention may comprise one or more additional enzymes, such as invertase (syn. beta-fructofuranosidase or beta-fructosidase), lactase (syn. beta-galactosidase), maltase (syn. alpha-glucosidase), alpha-amylase, beta-amylase, glucoamylase, pullulanase, isoamylase, amyloglucosidase, cyclomaltodextrin glucantransferase (CGTase). These enzymes have the property of releasing fructose and/or glucose from fructose and/or glucose containing substances and foodstuffs—alone or in combination with one or more of these enzymes—, whereby the enzymes pullulanase and isoamylase also increase the efficiency of glucoamylase and beta-amylase. All these enzymes are commercially available (e.g. BioCat Inc., Troy, USA or Novozymes A/S, Denmark or Amano Enzymes Inc., Japan or Sigma-Aldrich) and, up to now, have never been used in combination with 5-D-fructose dehydrogenase and glucose isomerase in the case of diabetes. Examples for agents according to the present invention include:

5-D-fructose dehydrogenase in combination with invertase, or 5-D-fructose dehydrogenase in combination with glucose isomerase and invertase, or 5-D-fructose dehydrogenase in combination with glucose isomerase and lactase and invertase, still further 5-D-fructose dehydrogenase in combination with glucose isomerase, Invertase, alpha amylase, beta amylase, glucoamylase, maltase, isoamylase and pullulanase (combination of 9 enzymes), or 5-D-fructose dehydrogenase in combination with glucose isomerase, alpha amylase, beta amylase, glucoamylase, maltase, isoamylase and pullulanase as well as invertase and lactase (combination of 10 enzymes).

For example, said invertase can release glucose from e.g. sucrose and lactase can release glucose from lactose. Beta-amylase breaks down e.g. 1,4-alpha-bonds in starch, starting at the non-reducing end of the polysaccharide chain with cleaving of maltose, and glucose is released by the action of maltase on maltose. By the addition of one or more of these enzymes to the agent according to the present invention, the endogenic release of glucose from glucose containing substances or foodstuffs, in particular from sucrose and starch, may also be promoted and accelerated, so that the conversion of glucose into fructose effected by the glucose isomerase and the conversion of fructose into 5-keto-D-fructose which is catalyzed by the 5-D-fructose dehydrogenase may occur earlier. Therefore, the addition of one or more of these enzymes to the agent according to the present invention may have the benefit of reducing the required amount of 5-D-fructose dehydrogenase and glucose isomerase.

The activity of invertase is measured in Sumner units (SU, assay available e.g. from Bio-Cat Inc., Troy, Va., USA). An SU is defined as the amount of the enzyme which converts 1 mg of sucrose into glucose and fructose under standard test conditions within 5 minutes at 20° C. and a pH value of 4.5. If the agent according to the present invention also contains invertase, the activity of the invertase per dose unit should be between 50 and 250,000 SU, preferably between 100 and 150.000 SU and particularly preferably between 150 and 100,000 SU per dose unit.

The activity of lactase is given in Food Chemical Codex (FCC) units (assay is published in the Food Chemical Codex, fifth edition, and also available e.g. from Bio Cat Inc. Troy, Va. or Amano Enzymes, Japan or from Sigma Aldrich). If the agent according to the present invention also contains lactase, the activity of the lactase per dose unit should be between 50 and 200,000 FCC units, preferably between 100 and 100,000 FFC units and particularly preferably between 150 and 50,000 FCC units.

The activity of maltase is defined in units, wherein one unit is the amount of maltase which will convert maltose to D-glucose at a rate of one milligram per minute at 37° C. and a pH of 4.0 in a 10% maltose solution by weight.

Where the agent according to the present invention also contains maltase, the activity per dose unit should be between 100 and 100,000 units, preferably between 200 and 50,000 units and particularly preferably between 500 and 20,000 units Also for the other enzymes mentioned, the standard test conditions and the way in which the enzyme activities are to be determined are known and can be read up by specialists in the field.

Insofar as one or more of the optional enzymes are added to the agent according to the present invention, they—as is the case for the 5-D-fructose dehydrogenase and the glucose isomerase—should be used in sufficient amounts so that they can develop a sufficient enzyme activity for the intended purpose, e.g. sufficient invertase, so that an amount of sucrose usually ingested with a normal meal (e.g. 15 g) can be cleaved, and/or lactase, so that an amount of lactose usually ingested with a normal meal (e.g. 10 g) can be cleaved.

The enzymes used can be for example in solid form, e.g. as crystalline or amorphous granules or powders, as a paste or as a liquid, as well as in other forms. In some embodiments, the enzyme is a free enzyme. In other embodiments, the enzyme may e.g. be immobilized on substrate, which can be powderized if necessary before the enzyme is used in accordance with the invention.

If the agent according to the present invention is added to a foodstuff before consumption or during production, the activity of 5-D-fructose dehydrogenase should be between 10 and 250,000 units, preferably between 25 and 150,000 units and particularly preferably between 50 and 100,000 units per gram of fructose and glucose combined contained in the foodstuff and the activity of the glucose isomerase should be between 0.01 and 20,000 GIU, preferably between 0.05 and 10,000 GIU and particularly preferably between 0.1 and 1000 GIU per gram of glucose in the foodstuff.

It may be advantageous to add an electron acceptor to the agent according to the present invention at e.g. a ratio (acceptor:substrate) of 1:1 to 1:1,000, preferably at a ratio of 1:2 to 1:200, particularly preferably at a ratio of 1:10 to 1:50. Examples of suitable acceptors which may be used include NAD+, NADP+, FAD+, vitamins, such as vitamin C, vitamin E or vitamin A, ferricyanide, ketones, aldehydes, 2,6-dichlorophenolindophenol, phenazine methosulfate, nitroblue tetrazolium (including mixtures thereof), but are not limited thereto.

The physiologically present electrolytes should be sufficient for the function of glucose isomerase. But it may also be advantageous to add electrolytes to the agent according to the present invention, e.g. in an amount of 0.0001% to 0.1% of the substrate (glucose). Examples of electrolytes include, but are not limited to, $MgSO_4$, $Na_2CO_3$, $NaHCO_3$, NaOH, $Na_2SO_4$, $MgCO_3$, $H_2SO_4$, $NaS_2O_3$, $NaS_2O_5$ (including mixtures thereof).

It may also be advantageous to add metal ions, especially cations, such as $Mn^{2+}$, $Mg^{2+}$, $Ca^{2+}$, $Zn^{2+}$, $Fe^{2+}$, $Co^{2+}$ or $Cu^{2+}$, including mixtures thereof, to the agent according to the present invention, namely preferably in a molar ratio of $10^{-6}$ to $10^{-2}$. For the above mentioned (xylose) glucose isomerase which is described by Yamanaka, especially $Mn^{2+}$ is a suitable cation.

Capsule sizes mentioned below refer to the size definitions used by Capsugel Belgium BVBA, Bornem, Belgium. The size of the capsules should be chosen according to the specific formulation of the agent.

A composition according to the present invention for the production of capsules (e.g. of size 3) may consist of 55 mg of 5-D-fructose dehydrogenase with an activity of 1000 units/mg, 50 mg of glucose isomerase with an activity 1 GIU/mg and 55 mg of dicalcium phosphate per capsule.

A further example for a dosage form according to the present invention consists of capsules (size 00) that contain 165 mg of 5-D-Fructose dehydrogenase with an activity of 1000 units/mg, 150 mg of glucose isomerase with an activity of 1 GIU/mg and 155 mg of dicalcium phosphate per capsule.

In a further composition example, a capsule of size 0 may contain 250 mg of 5-D-fructose dehydrogenase with an activity of 90 units/mg and 20 mg of glucose isomerase with an activity of 1 GIU/mg and 50 mg of dicalcium phosphate.

A further example for the production of capsules of size 00 may contain 370 mg of 5-D-fructose dehydrogenase with an activity of 90 units/mg, 30 mg of glucose isomerase with an activity of 1 GIU/mg and 70 mg of dicalcium phosphate.

Another example for the dosage form according to the present invention consists of capsules of size 00 which contain 110 mg of 5-D-fructose dehydrogenase with an activity of 500 units/mg, 50 mg of glucose isomerase with an activity of 1 GIU/mg, 100 mg of invertase with an activity of 200 SU units/mg, 90 mg of lactase with an activity of 100 FCC units/mg and 120 mg of dicalcium phosphate.

The invention may for example contain between 10 and 5 million units of 5-D-fructose dehydrogenase and between 0.01 and 100,000 GIU (=glucose isomerase units) of glucose isomerase per dose unit. In addition, suitable additives may be used in the required amount.

The invention may be provided for medical purposes and non-medical purposes, e.g. as a pharmaceutical composition, medical device, foodstuff or special foodstuff.

With the agent according to the present invention, afflictions and impairments of health that are caused by diabetes in its various degrees of severity can be significantly reduced or eliminated. The invention disclosed herein is especially suitable for the therapeutic treatment of diabetes. It is also suitable for use in methods for the therapeutic treatment of the human or animal body in which an uncontrolled increase in the level of blood sugar is to be prevented or a decrease in the level of blood sugar is intended.

In the description and claims, the term "glucose equivalent-containing" refers to all substances and foodstuffs that contain glucose (a) as glucose per se, (b) in a form from which glucose can be released in the digestive tract (e.g. by cleavage as glucose from a saccharide chain containing at least two saccharide monomers, such as sucrose), (c) in a form that can be converted to glucose, e.g. as fructose per se, or (d) in a form that can be released in the digestive tract and converted to glucose, e.g. as a saccharide chain containing at least two saccharide monomers, at least one of which can be cleaved from the saccharide chain as fructose.

In the description and claims, the term "total glucose" refers to the total content of glucose in a foodstuff (a) as glucose per se, (b) in a form from which glucose can be released in the digestive tract (e.g. by cleavage as glucose from a saccharide chain containing at least two saccharide monomers, such as sucrose), (c) in a form that can be converted to glucose, e.g. as fructose per se, or (d) in a form that can be released in the digestive tract and converted to glucose, e.g. a saccharide chain containing at least two saccharide monomers, at least one of which can be cleaved from the saccharide chain as fructose.

In the description and claims, the term "effective glucose content" of an item refers to the effective amount of total glucose in that item, taking into account the prior action of glucose and fructose converting enzymes that have been added and the future action of glucose and fructose converting enzymes that have been added to the item. Thus, for example, a foodstuff having a given glucose content and having microencapsulated glucose isomerase and microencapsulated 5-D-fructose dehydrogenase incorporated therein will have a lower effective glucose content than a foodstuff which lacks the microencapsulated glucose isomerase and 5-D-fructose dehydrogenase but is otherwise identical, since release of the glucose isomerase and 5-D-fructose dehydrogenase after ingestion will result in at least a portion of the glucose in the foodstuff being converted to 5-keto D-fructose.

In the description and claims, the term "total fructose" refers to the total content of fructose in a foodstuff (a) as fructose per se, (b) in a form from which fructose can be released in the digestive tract (e.g. by cleavage as fructose from a saccharide chain containing at least two saccharide monomers), (c) in a form that can be converted to fructose, e.g. as glucose per se, or (d) in a form that can be released in the digestive tract and converted to fructose, e.g. a saccharide chain containing at least two saccharide monomers, at least one of which can be cleaved from the saccharide chain as glucose.

Thus, there is provided, in accordance with embodiments of the invention, the use of glucose isomerase in combination with 5-D-fructose dehydrogenase and optionally in combination with one or more enzyme(s) selected from invertase, lactase, maltase, alpha-amylase, beta-amylase, glucoamylase, pullulanase, isoamylase, amyloglucosidase and cyclomaltodextrin glucanotransferase for production of an agent, preferably a pharmaceutical composition, for the curative or prophylactic treatment of diabetes, the diagnosis of diabetes, for reducing the bioavailability of glucose and/or fructose in the human or animal body, for reducing the glucose content and/or the fructose content in a foodstuff, or for preventing or at least reducing an increase of the level of blood glucose after the intake of glucose containing food. In some embodiments, the agent is selected from a pharmaceutical composition, a medical device, a foodstuff or a special foodstuff. In some embodiments, the agent is in a form for oral use. In some embodiments, the enzymes are protected by a coating to be stable at pH values of less than 4, preferably less than 3. In some embodiments, the agent is suited to be added to food at the production stage of the same and/or before eating. In some embodiments, the agent is in a form for use in immobilised form.

There is also provided, in accordance with embodiments of the invention, a process for the treatment of a foodstuff, comprising the steps of contacting the foodstuff with glucose isomerase in combination with 5-D-fructose dehydrogenase and optionally in combination with one or more enzyme(s) selected from invertase, lactase, maltase, alpha-amylase, beta-amylase, glucoamylase, pullulanase, isoamylase, amyloglucosidase and cyclomaltodextrin glucanotransferase and initiating the reduction of the glucose content and/or fructose content of the foodstuff. In some embodiments, as a further step prior to the initiation, ingestion of the foodstuff takes place.

There is also provided, in accordance with embodiments of the invention, a mammalian-ingestible composition of matter which comprises a plurality of enzymes that collectively convert D-glucose into a first form that is at least one of (a) biologically inactive in a chosen mammalian body, (b) not digestible in the digestive tract of the mammalian body and (c) not metabolizable in the mammalian body. In some embodiments, the plurality of enzymes collectively converts D-glucose into a second non-glucose form and converts the non-glucose form into the first form. In some embodiments, the second non-glucose form is D-fructose. In some embodiments, the chosen mammalian body is a human body. In some embodiments, the chosen mammalian body is a non-human body. In some embodiments, the plurality of enzymes collectively converts D-glucose to 5-keto-D-fructose. In some embodiments, the first form is 5-keto-D-fructose. In some embodiments, at least one of the plurality of enzymes is a glucose isomerase. In some embodiments, the glucose isomerase is a xylose isomerase. In some embodiments, at least one of the plurality of enzymes is 5-D-fructose dehydrogenase. In some embodiments, the composition of matter is a human dietary supplement or a pharmaceutical composition. In some embodiments, the composition of matter is an animal dietary supplement or a veterinary composition. In some embodiments, the composition of matter is a special foodstuff. In some embodiments, the composition of matter further comprises at least one pharmaceutically or dietarily acceptable carrier or excipient. In some embodiments, the composition of matter further comprises at least one veterinarily acceptable carrier or excipient. In some embodiments, the composition of matter contains each enzyme of the plurality of enzymes in microencapsulated form. In some embodiments, the composition of matter is in the form of a capsule or tablet. In some embodiments, the composition of matter is in the form of granules or pellets. In some embodiments, the composition of matter is in the form of a solution. In some embodiments, the composition of matter is in the form of a liquid. In some embodiments, the composition of matter is in the form of a gel or suspension. In some embodiments, the composition of matter is in the form of a gelcap. In some embodiments, the composition of matter is in the form of a powder.

There is also provided, in accordance with embodiments of the invention, a composition of matter which is microencapsulated enzyme glucose isomerase.

There is also provided, in accordance with embodiments of the invention, a composition of matter which is a mixture of microencapsulated glucose isomerase and microencapsulated 5-D-fructose dehydrogenase. In some embodiments, the glucose isomerase and the 5-D-fructose dehydrogenase are microencapsulated together. In some embodiments, the glucose isomerase and the 5-D-fructose dehydrogenase are separately microencapsulated.

In some embodiments, the composition of matter as described above is adapted to be mixed with a food.

There is also provided, in accordance with embodiments of the invention, a composition of matter comprising the enzymes glucose isomerase and 5-D-fructose dehydrogenase admixed with a mammalian-ingestible substance. In some embodiments, the mammalian-ingestible substance is a human-ingestible substance. In some embodiments, the mammalian-ingestible substance is an animal-ingestible substance. In some embodiments, the mammalian-ingestible substance is a pharmaceutically or dietarily acceptable carrier or excipient. In some embodiments, the mammalian-ingestible substance is a veterinarily acceptable carrier or excipient. In some embodiments, at least one of the glucose isomerase and the 5-D-fructose dehydrogenase is microencapsulated. In some embodiments, both the glucose isomerase and the 5-D-fructose dehydrogenase are microencapsulated.

In some embodiments, the plurality of enzymes in the composition of matter as described above constitutes between 5 and 99.9% by weight of the composition of matter. In some embodiments, the plurality of enzymes constitutes between 10 and 80% by weight of the composition of matter. In some embodiments, the plurality of enzymes constitutes between 25 and 60% by weight of the composition of matter.

In some embodiments, the composition of matter as described above is in unit dosage form and the unit dosage contains between 10 and 5 million units of 5-D-fructose dehydrogenase activity. In some embodiments, the unit dosage contains between 25 and 2.5 million units of 5-D-fructose dehydrogenase activity. In some embodiments, the unit dosage contains between 50 and 1 million units of 5-D-fructose dehydrogenase activity.

In some embodiments, the composition of matter as described above is in unit dosage form and each dosage unit contains 0.01 to 100,000 units of glucose isomerase activity per dose unit. In some embodiments, each dosage unit contains 0.05 to 10,000 units of glucose isomerase activity per dose unit. In some embodiments, each dosage unit contains 0.1 to 1,000 units of glucose isomerase activity per dose unit. In some embodiments, the glucose isomerase is a xylose isomerase.

In some embodiments, the composition of matter as described above further comprises at least one of an electrolyte and a metal ion. In some embodiments, the electrolyte is selected from the group consisting of $MgSO_4$, $Na_2CO_3$, $NaHCO_3$, $NaOH$, $Na_2SO_4$, $MgCO_3$, $H_2SO_4$, $NaS_2O_3$, $NaS_2O_5$ and mixtures thereof. In some embodiments, the metal ion is selected from the group consisting of $Mn^{2+}$, $Mg^{2+}$, $Ca^{2+}$, $Zn^{2+}$, $Fe^{2+}$, $Co^{2+}$, $Cu^{2+}$ and mixtures thereof.

In some embodiments, the composition of matter as described above comprises a coating which dissolves in an aqueous medium at a pH of between 3.0 and 8.0. In some embodiments, the coating does not dissolve in an aqueous medium at a pH of below 3.0. In some embodiments, the coating does not dissolve in an aqueous medium at a pH below 4.0. In some embodiments, the coating does not dissolve in an aqueous medium at a pH above 6.5. In some embodiments, the coating does not dissolve in an aqueous medium at a pH above 6.0.

In some embodiments, the composition of matter as described above is a slow-release or extended-release formulation. In some embodiments, the slow-release or extended-release formulation comprises a slow-release or extended-release coating.

In some embodiments, the composition of matter as described above further comprises at least a third enzyme. In some embodiments, the third enzyme is capable of cleaving fructose or glucose from a sugar that contains at least two saccharide monomers. In some embodiments, the third enzyme is invertase or maltase. In some embodiments, the third enzyme is invertase, the composition of matter is in unit dosage form, and each unit dosage contains between 50 and 250,000 Sumner units of invertase activity. In some embodiments, each unit dosage contains between 100 and 150,000 Sumner units of invertase activity. In some embodiments, each unit dosage contains between 150 and 100,000 Sumner units of invertase activity. In some embodiments, the third enzyme is maltase, the composition of matter is in unit dosage form, and each unit dosage contains between 100 and 100,000 units of maltase activity. In some embodiments, each unit dosage contains between 200 and 50,000 units of maltase activity. In some embodiments, each unit dosage contains between 500 and 20,000 units of maltase activity. In some embodiments, the composition of matter comprises both invertase and maltase.

In some embodiments, the composition of matter as described above further comprises one or more members of the group consisting of lactase, alpha-amylase, beta-amylase, glucoamylase, pullulanase, isoamylase, amyloglucosidase and cyclomaltodextrin glucantransferase (CGTase). In some embodiments, the member is lactase, the composition of matter is in unit dosage form and each dosage unit contains 50 to 200,000 FCC units of lactase activity per dose unit. In some embodiments, each dosage unit contains 100 to 100,000 FCC units of lactase activity per dose unit. In some embodiments, each dosage unit contains 150 to 50,000 units of lactase activity per dose unit.

In some embodiments, the composition of matter as described above is a foodstuff, and the plurality of enzymes is in active form. In some embodiments, the amount or concentration of at least one enzyme in the plurality of enzymes in the foodstuff is greater than the naturally occurring concentration or amount of the enzyme in the foodstuff. In some embodiments, the foodstuff is a glucose equivalent-containing foodstuff. In some embodiments, the foodstuff is a fructose-containing foodstuff. In some embodiments, the foodstuff is a glucose-containing foodstuff. In some embodiments, the foodstuff is a glucose-containing foodstuff and contains glucose isomerase in an amount of 0.01 to 20,000 units of activity per gram of total glucose in the foodstuff. In some embodiments, the glucose isomerase is present in an amount of 0.05 to 10,000 units of activity per gram of total glucose in the foodstuff. In some embodiments, the glucose isomerase is present in an amount of 0.1 to 1,000 units of activity per gram of total glucose in the foodstuff. In some embodiments, at least one of the enzymes is 5-D-fructose dehydrogenase which is present in an amount of 10 to 250,000 units of activity per gram of total fructose in the foodstuff. In some embodiments, the 5-D-fructose dehydrogenase is present in an amount of 25 to 150,000 units of activity per gram of total fructose in the foodstuff. In some embodiments, the 5-D-fructose dehydrogenase is present in an amount of 50 to 100,000 units of activity per gram of total fructose in the foodstuff. In some embodiments, the foodstuff is a foodstuff which has been baked. In some embodiments, the foodstuff is a foodstuff which has been cooked. In some embodiments, the foodstuff is a liquid, paste or broth. In some embodiments, the plurality of enzymes is present in microencapsulated form. In some embodiments, at least one of the plurality of enzymes is 5-D-fructose dehydrogenase. In some embodiments, the concentration or amount of the 5-D-fructose dehydrogenase in the foodstuff is greater than the naturally occurring concentration or amount of 5-D-fructose dehydrogenase in the foodstuff. In some embodiments, at least one of the enzymes of the plurality of enzymes is a glucose isomerase. In some embodiments, the concentration or amount of the glucose isomerase in the foodstuff is greater than the naturally occurring concentration or amount of the glucose isomerase in the foodstuff. In some embodiments, the glucose isomerase is a xylose isomerase. In some embodiments, the foodstuff further contains at least one third enzyme in active form. In some embodiments, the concentration or amount of the third enzyme in the foodstuff is greater than the naturally occurring concentration or amount of the third enzyme in the foodstuff. In some embodiments, the third enzyme is selected from the group consisting of invertase, maltase, lactase, alpha-amylase, beta-amylase, glucoamylase, pullulanase, isoamylase, amyloglucosidase and cyclomaltodextrin glucantransferase (CGTase) or a mixture thereof. In some embodiments, the third enzyme is invertase. In some embodiments, the third enzyme is maltase. In some embodiments, the third enzyme is lactase. In some embodiments, the third enzyme is alpha-amylase. In some embodiments, the third enzyme is beta-amylase. In some embodiments, the third enzyme is glucoamylase. In some embodiments, the third enzyme is pullulanase. In some embodiments, the third enzyme is isoamylase. In some embodiments, the third enzyme is amyloglucosidase. In some embodiments, the third enzyme is CGTase. In some embodiments, the composition further comprises at least one of an electrolyte and a metal ion. In some embodiments, the electrolyte is selected from the group consisting of $MgSO_4$, $Na_2CO_3$, $NaHCO_3$, $NaOH$, $Na_2SO_4$, $MgCO_3$, $H_2SO_4$, $NaS_2O_3$, $NaS_2O_5$ and mixtures thereof. In some embodiments, the metal ion is selected from the group consisting of $Mn^{2+}$, $Mg^{2+}$, $Ca^{2+}$, $Zn^{2+}$, $Fe^{2+}$, $Co^{2+}$, $Cu^{2+}$ and mixtures thereof. In some embodiments, the third enzyme is a mixture of at least invertase and maltase. In some embodiments, the third enzyme is a mixture of at least two of the group of invertase, maltase, lactase, amylase, beta-amylase, glucoamylase, pullulanase, isoamylase, amyloglucosidase and CGTase. In some embodiments, the third enzyme is in microencapsulated form. In some embodiments, the composition of matter as described above is a foodstuff which is not a dough.

In some embodiments, none of the enzymes in the plurality of enzymes in the composition of matter described above is contained in an inorganic-based sol-gel biocompatible matrix. In some embodiments, none of the enzymes in the composition of matter is contained in an inorganic-based sol-gel biocompatible matrix.

In some embodiments, the composition of matter described above is substantially free of substances which are not approved for oral human ingestion.

In some embodiments, the composition of matter described above is substantially free of substances which are not approved for oral non-human mammal ingestion.

In some embodiments, the composition of matter described above is adapted for oral ingestion.

In some embodiments, the composition of matter described above comprises an electron acceptor. In some embodiments, the electron acceptor is selected from the group consisting of Nicotinamide Adenine Dinucleotide$^+$ (NAD$^+$), nicotinamide adenine dinucleotide phosphate+ (NADP$^+$), flavin adenine dinucleotide$^+$ (FAD$^+$), vitamin C, E or A, ferricyanide, ketones, aldehydes, 2,6-di-chloro-phenolindophenol, phenazine methsulfate and mixtures thereof. In some embodiments, the molar ratio of electron acceptor to total fructose is from 1:1 to 1:1000. In some embodiments, the molar ratio of electron acceptor to total fructose is from 1:2 to 1:200. In some embodiments, the molar ratio of electron acceptor to total fructose is from 1:10 to 1:50. In some embodiments, the molar ratio of electron acceptor to fructose is from 1:1 to 1:1000. In some embodiments, the molar ratio of electron acceptor to fructose is from 1:2 to 1:200. In some embodiments, the molar ratio of electron acceptor to fructose is from 1:10 to 1:50.

In some embodiments, the composition of matter described above further comprises one or more enzyme stabilizers. In some embodiments, the enzyme stabilizer stabilizes 5-D-fructose dehydrogenase. In some embodiments, the enzyme stabilizer stabilizes a glucose isomerase.

There is also provided, in accordance with embodiments of the invention, a method of (i) reducing the effect of diabetes on a mammalian subject body, (ii) reducing the effect of D-glucose on a mammalian subject body, or (iii) reducing the effect of total glucose on a mammalian subject body, comprising administering to a mammalian subject an efficacious amount of a plurality of enzymes that collectively converts D-glucose to a first form that is at least one of (a) biologically inactive in the subject body, (b) not digestible in the subject digestive tract and (c) not metabolizable in the subject body. In some embodiments, the plurality of enzymes collectively converts D-glucose to a second non-glucose form and convert the second non-glucose form to the first form. In some embodiments, the plurality of enzymes includes a glucose isomerase. In some embodiments, the glucose isomerase is a xylose isomerase. In some embodiments, the plurality of enzymes includes 5-D-fructose dehydrogenase. In some embodiments, the mammalian subject is a human subject. In some embodiments, the mammalian subject is a non-human subject. In some embodiments, the administering comprises administering a mammalian-ingestible composition of matter as described above. In some embodiments, the effect of D-glucose or total glucose is a deleterious effect on the health of the mammal. In some embodiments, the effect of D-glucose or total glucose is hyperglycemia. In some embodiments, the effect of D-glucose or total glucose is diabetic coma. In some embodiments, the effect of D-glucose or total glucose is a complication of diabetes. In some embodiments, the complication of diabetes is selected from the group consisting of diabetic angiopathy, macroangiopathy, coronary heart disease, microangiopathy, retinopathia diabetica, maculopathy, nephropathia diabetica, gangrene, Gastroparesis diabeticorum, impaired function of the small intestine, constipation, stool incontinence, diabetic neuropathy, diabetic autonome neuropathy and diabetic foot. In some embodiments, the composition of matter is administered prior to eating. In some embodiments, the composition of matter is administered immediately prior to eating. In some embodiments, the composition of matter is administered concurrently with a meal. In some embodiments, the composition of matter is administered after eating. In some embodiments, the composition of matter is administered immediately after eating. In some embodiments, the second non-glucose form is D-fructose. In some embodiments, the first form is 5-keto-D-fructose. In some embodiments, the method is part of a program of therapeutic treatment or management of diabetes. In some embodiments, the diabetes is diabetes type I. In some embodiments, the diabetes is LADA diabetes (latent autoimmune diabetes in adults). In some embodiments, the diabetes is diabetes type II. In some embodiments, the diabetes is pregnancy-induced diabetes. In some embodiments, the diabetes is impaired glucose tolerance. In some embodiments, the diabetes is a minor disorder of blood sugar metabolism. In some embodiments, the method further comprises administering to the subject at least one third enzyme selected from the group consisting of invertase, maltase, lactase, alpha-amylase, beta-amylase, glucoamylase, pullulanase, isoamylase, amyloglucosidase and cyclomaltodextrin glucantransferase (CGTase) or a mixture thereof.

There is also provided, in accordance with embodiments of the invention, a kit comprising a plurality of enzymes that collectively converts D-glucose into a first form that is at least one of (a) biologically inactive in a chosen mammalian body, (b) not digestible in the digestive tract of the mammalian body and (c) not metabolizable in the mammalian body, and instructions explaining how to use the plurality of enzymes to reduce the effects of glucose in the mammalian body. In some embodiments, the plurality of enzymes collectively converts D-glucose into a second non-glucose form and converts the second non-glucose form to the first form. In some embodiments, the instructions explain how to use the plurality of enzymes to reduce the effects of total glucose in the mammalian body. In some embodiments, the mammalian body is the human body. In some embodiments, the mammalian body is a non-human body. In some embodiments, the plurality of enzymes is present as a composition of matter as described above. In some embodiments, the plurality of enzymes collectively converts D-glucose into 5-keto-D-fructose. In some embodiments, one of the plurality of enzymes is 5-D-fructose dehydrogenase. In some embodiments, one of the plurality of enzymes is a glucose isomerase. In some embodiments, the glucose isomerase is a xylose isomerase. In some embodiments, the kit further comprises at least one third enzyme. In some embodiments, the third enzyme is selected from the group consisting of invertase, maltase, lactase, alpha-amylase, beta-amylase, glucoamylase, pullulanase, isoamylase, amyloglucosidase and cyclomaltodextrin glucantransferase (CGTase) or a mixture thereof. In some embodiments, the instructions further explain how to use the third enzyme or mixture thereof in conjunction with the plurality of enzymes.

There is also provided, in accordance with embodiments of the invention, a reduced-total glucose foodstuff. In some embodiments, the foodstuff is a reduced-fructose foodstuff. In some embodiments, the foodstuff is a reduced-glucose foodstuff.

There is also provided, in accordance with embodiments of the invention, a method for preparing a reduced-total glucose foodstuff, comprising contacting a foodstuff or foodstuff precursor with a plurality of enzymes that collectively converts D-glucose into a first form that is at least one of (a) biologically inactive in a chosen mammalian body, (b) not digestible in the digestive tract of the mammalian body and (c) not metabolizable in the mammalian body, and completing any additional steps necessary to prepare the foodstuff. In some embodiments, the plurality of enzymes collectively converts D-glucose to a second non-glucose form and converts the non-glucose form to the first form. In some embodiments, the second non-glucose form is D-fructose. In some embodiments, the first form is 5-D-ketofructose. In some embodiments, the mammalian body is a human body. In some embodiments, the mammalian body is a non-human body. In some embodiments, one of the plurality of enzymes is a glucose isomerase. In some embodiments, one of the plurality of enzymes is 5-D-fructose dehydrogenase. In some embodiments, the foodstuff is not a baked foodstuff. In some embodiments, the foodstuff is not bread. In some embodiments, the foodstuff is not a dough. In some embodiments, the plurality of enzymes collectively converts D-glucose to 5-keto-D-fructose. In some embodiments, the method also comprises contacting the foodstuff or foodstuff precursor with a third enzyme that cleaves glucose from saccharide chains having at least two saccharide monomers. In some embodiments, the third enzyme is invertase, maltase or a mixture thereof. In some embodiments, the method also comprises contacting the foodstuff or foodstuff precursor with an additional enzyme that cleaves fructose from saccharide chains having at least two saccharide monomers. In some embodiments, the method also comprises contacting the foodstuff or foodstuff precursor with a member of the group consisting of lactase, alpha-amylase, beta-amylase, glucoamylase, pullulanase, isoamylase, amyloglucosidase and cyclomaltodextrin glucantransferase (CGTase) or a mixture thereof.

There is also provided, in accordance with embodiments of the invention, a method for preparing a foodstuff or foodstuff precursor having a reduced effective glucose content, comprising incorporating into the foodstuff or foodstuff precursor a plurality of enzymes that collectively convert D-glucose into a first form that is at least one of (a) biologically inactive in a chosen mammalian body, (b) not digestible in the digestive tract of the mammalian body and (c) not metabolizable in the mammalian body, and completing any additional steps necessary to prepare the foodstuff, wherein the plurality of enzymes is incorporated in such manner that the plurality of enzymes will convert the D-glucose to the first form after ingestion of the foodstuff. In some embodiments, at least one of the plurality of enzymes is 5-D-fructose dehydrogenase. In some embodiments, at least one of the plurality of enzymes is a glucose isomerase. In some embodiments, the glucose isomerase is a xylose isomerase. In some embodiments, the foodstuff is not a baked foodstuff. In some embodiments, the foodstuff is not bread. In some embodiments, the foodstuff or foodstuff precursor is not a dough. In some embodiments, the plurality of enzymes collectively converts D-glucose to 5-keto-D-fructose. In some embodiments, each enzyme in the plurality of enzymes is microencapsulated. In some embodiments, the method further comprises incorporating into the foodstuff or foodstuff precursor at least one third enzyme in a manner that the third enzyme will be active in the mammalian body after ingestion therein. In some embodiments, the third enzyme is selected from the group consisting of invertase, maltase, lactase, alpha-amylase, beta-amylase, glucoamylase, pullulanase, isoamylase, amyloglucosidase and cyclomaltodextrin glucantransferase (CGTase) or a mixture thereof. In some embodiments, the third enzyme is at least one of maltase and invertase. In some embodiments, the third enzyme is a mixture of maltase and invertase. In some embodiments, at least one third enzyme cleaves glucose from saccharide chains having at least two saccharide monomers. In some embodiments, at least one third enzyme cleaves fructose from saccharide chains having at least two saccharide monomers. In some embodiments, each third enzyme is microencapsulated.

In some embodiments, in the methods described above one of the plurality of enzymes is 5-D-fructose dehydrogenase which is present in an amount of 10 to 250,000 units of activity per gram of total fructose in the foodstuff or foodstuff precursor. In some embodiments, the 5-D-fructose dehydrogenase is present in an amount of 25 and 150,000 units of activity per gram of total fructose in the foodstuff or foodstuff precursor. In some embodiments, the 5-D-fructose dehydrogenase is present in an amount of 50 to 100,000 units of activity per gram of total fructose in the foodstuff or foodstuff precursor. In some embodiments, the foodstuff or foodstuff precursor is a glucose-containing foodstuff or foodstuff precursor and contains glucose isomerase in an amount of 0.01 to 20,000 units of activity per gram of total glucose in the foodstuff or foodstuff precursor. In some embodiments, the glucose isomerase is present in an amount of 0.05 to 10,000 units of activity per gram of total glucose in the foodstuff or foodstuff precursor. In some embodiments, the glucose isomerase is present in an amount of 0.1 to 1,000 units of activity per gram of total glucose in the foodstuff or foodstuff precursor. In some embodiments, the method further comprises incorporating into the foodstuff or foodstuff precursor at least one further enzyme or mixture of enzymes in a manner that the further enzyme or mixture of enzymes will be active before ingestion of the foodstuff. In some embodiments, the further enzyme is selected from the group consisting of invertase, maltase, lactase, alpha-amylase, beta-amylase, glucoamylase, pullulanase, isoamylase, amyloglucosidase and cyclomaltodextrin glucantransferase (CGTase) or a mixture thereof. In some embodiments, the further enzyme is at least one of invertase and maltase. In some embodiments, the further enzyme is a mixture of maltase and invertase. In some embodiments, the further enzyme or mixture of enzymes is the same as the third enzyme or mixture of enzymes. In some embodiments, the further enzyme or mixture of enzymes is different than the third enzyme or mixture of enzymes. In some embodiments, the further enzymes include a further group of enzymes which is the same as the plurality of enzymes.

In some embodiments, the mammalian body is a human body. In some embodiments, the mammalian body is a non-human body.

The invention claimed is:

1. A method of treating diabetes or reducing the amount of absorbed glucose in a mammalian body, comprising administering to a mammalian subject in need of such treatment or reduction an efficacious amount of a combination of 5-D-fructose dehydrogenase and a glucose isomerase.

2. The method according to claim 1, further comprising administering to said subject a third enzyme selected from the group consisting of invertase, maltase, lactase, alpha-amylase, beta-amylase, glucoamylase, pullulanase, isoamylase, amyloglucosidase, cyclomaltodextrin glucanotransferase and combinations thereof.

3. The method according to claim 1, wherein said 5-D-fructose dehydrogenase is administered in sufficient temporal proximity to eating to enable the glucose isomerase to exert its converting effect on glucose in the food after ingestion.

4. The method according to claim 3, wherein said glucose isomerase is administered in sufficient temporal proximity to eating to enable the glucose isomerase to exert its converting effect on glucose in the food after ingestion.

5. The method according to claim 1, wherein said administration is oral administration.

6. The method according to claim 1 wherein said method is part of a program of therapeutic treatment or management of diabetes.

7. A method according to claim 1, wherein said diabetes is accompanied by a condition selected from the group consisting of diabetic angiopathy, macroangiopathy, coronary heart disease, microangiopathy, retinopathia diabetica, maculopathy, nephropathia diabetica, gangrene, Gastroparesis diabeticorum, impaired function of the small intestine, constipation, stool incontinence, diabetic neuropathy, diabetic autonome neuropathy and diabetic foot.

8. The method according to claim 1, wherein said diabetes is selected from the group consisting of diabetes type I, LADA diabetes (latent autoimmune diabetes in adults), diabetes type II, and pregnancy-induced diabetes.

9. A method of reducing the incidence of hyperglycemia in a mammalian body, comprising administering to a mammalian subject in need of such reduction an efficacious amount of a combination of 5-D-fructose dehydrogenase and a glucose isomerase.

\* \* \* \* \*